United States Patent [19]
Yamamoto et al.

[11] Patent Number: 5,463,465
[45] Date of Patent: Oct. 31, 1995

[54] APPARATUS FOR EXAMINING THE EXTERNAL APPEARANCE OF SOLID ARTICLES

[75] Inventors: Taizo Yamamoto, Osaka; Hirokazu Konishi, Sakurai; Yoshihisa Kawaguchi, Kashihara; Akira Nagao, Tenri, all of Japan

[73] Assignee: Japan Elanco Company Limited, Osaka, Japan

[21] Appl. No.: 272,571

[22] Filed: Jul. 11, 1994

[30] Foreign Application Priority Data

Jul. 16, 1993 [JP] Japan .................................. 5-176407

[51] Int. Cl.⁶ .................. G01B 11/00; G01N 21/84; B07C 5/00; B07C 5/342
[52] U.S. Cl. .................. 356/394; 356/426; 356/428; 356/237; 209/577; 209/587; 209/939
[58] Field of Search .................. 356/426–428, 356/394, 237; 209/576–577, 587, 939

[56] References Cited

U.S. PATENT DOCUMENTS

| | | | |
|---|---|---|---|
| 3,757,943 | 9/1973 | Chae et al. | 356/427 |
| 3,920,541 | 11/1975 | VandenBerg et al. | 209/587 |
| 4,354,602 | 10/1982 | Miyoshi et al. | 209/577 |
| 4,584,817 | 4/1986 | Yamamoto et al. | 53/329.2 |
| 4,731,979 | 3/1988 | Yamamoto et al. | 53/529 |
| 4,872,564 | 10/1989 | van der Schoot | 356/426 |
| 5,186,887 | 2/1993 | Yaginuma | 356/426 |

FOREIGN PATENT DOCUMENTS

| | | |
|---|---|---|
| 54-18955 | 7/1979 | Japan . |
| 58-1636 | 1/1983 | Japan . |
| 61-211213 | 9/1986 | Japan . |
| 62-229050 | 10/1987 | Japan . |
| 2-946 | 1/1990 | Japan . |
| 5-69934 | 3/1993 | Japan . |

OTHER PUBLICATIONS

"Webster II New Riverside University Dictionary", The Riverside Publishing Company, 1988, pp. 201, 407 1017.

*Primary Examiner*—F. L. Evans
*Assistant Examiner*—Jason D. Eisenberg
*Attorney, Agent, or Firm*—Fish & Richardson

[57] ABSTRACT

In an appearance examination apparatus for solid article such as capsules, tablets and the like, the solid articles are all oriented in the horizontal direction in the same manner in a plurality of feeding lines while they are transferred from a hopper to a feeding drum, a first restriction drum and a second restriction drum. The solid articles are continuously supplied to an examination drum which intermittently rotates at predetermined time intervals. The solid articles are held in predetermined positions between first and second examination rollers and are always rotated. An image pick-up device observes the entire surface of the solid articles and the inferior articles are removed.

8 Claims, 6 Drawing Sheets

APPARATUS FOR EXAMINING THE EXTERNAL APPEARANCE OF SOLID ARTICLES

BACKGROUND OF THE INVENTION

This invention relates to an appearance examination apparatus for solid articles which have a rotationally symmetrical shape such as a hard-type or soft-type capsule, a Rugby ball shaped or sphere tablet, and the like.

DESCRIPTION OF RELATED ART

A conventional appearance examination apparatus for solid articles, which is shown in Publication Gazette of Examined Japanese Patent Application She 54-18955 is described referring to FIG. 5. In FIG. 5, an examination head 200 is intermittently rotated around its rotation axis on a horizontal plane. A plurality of rollers 201 are provided in the vicinity of an outer periphery of the examination head 200. The rollers 201 are rotated in the counterclockwise direction around their rotation axes 202 as shown by arrow B. Solid articles 1 are conveyed in the vertical direction by buckets 220 which are driven by a chain mechanism. When bucket 220, which conveys the solid article 1, reaches the same horizontal plane as the examination head 200, a plunger 221 pushes the solid article 1 in the direction shown by arrow D. Thus, the solid article 1 is transferred to the examination head 200 from the bucket 220. In the examination head 200, air is removed by a vacuum in the direction shown by arrow A; so that the solid article 1 is held between two adjacent rollers 201. Since the rollers 201 rotate in the counterclockwise direction as shown by arrow B, the solid article 1 receives reaction forces from the rollers 201. Thereby, the solid article 1 rotates in the clockwise direction as shown by arrow C.

When the solid article 1 reaches predetermined position X, a light beam is emitted from a light source 203. Reflected light 204 from the solid article 1 is input to a photocell 208 through a slit 207 which has a predetermined shape corresponding to the basic shape of the solid articles 1. Suspended time of the examination head 200 is set to be longer than the time that the solid article 1 needs for at least one rotation. Thus, the photocell 208 receives the reflected light from entire outer surface of the solid article. When the solid article 1 has no defect on its surface, the output level of the photocell 208 does not change. However, when an extraneous material is adhered to the surface of the solid article 1, or when the surface of the solid article 1 is uneven, the light reflected from these parts will change. Thus, the output of the photocell 208 will change. By detecting the change in the output of the photocell 208, the defective article can be found. When the defective solid article 1 reaches to the position of removing shoot 209, it is blown into the removing shoot 209 by compressed air from a nozzle 205. Thereby, the defective solid article is removed from the examination process. On the other hand, the normal solid articles 1 are blown into a pick-up shoot 210 by compressed air from another nozzle 206.

Next, a conventional arranging apparatus for solid articles such as capsules, which is used in the abovementioned conventional appearance examination apparatus for solid articles, is described referring to FIGS. 6(a), 6(b) and 6(c). FIG.6(a) shows a cross-section of the bucket 220 perpendicular to the conveying direction of the solid articles 1. FIGS. 6(b) and 6(c) show cross-sections of the buckets 220 parallel to the conveying direction of the solid articles 1.

In FIG. 6(a), the bucket 220 has an upper pocket part 220a and lower pocket part 220b. The upper pocket part 220a has a width a little wider than the diameter of a cap of a capsule 250. The lower pocket part 220b has a width which is a little wider than the diameter of a body of the capsule 250 but a little narrower than the diameter of the cap of the capsule 250. A guide rail 230 is provided in the the lower pocket part 220b.

In FIG. 6(b), the capsule 250 is held in the bucket 220 so that body 250b is positioned to the forward in the conveying direction as shown by arrow E. When the capsule 250 proceeds to cutting part 231 of the guide rail 230, it rotates about edge 250c of cap 250a by gravity and the vacuum shown by arrow F. Thus. the capsule stands up as designated by numeral 250b so that edge 250c contacts offset part 220c between the upper pocket part 220a and the lower pocket part 220b. The capsule 250 is conveyed in the bucket, the body 250b contacts the guide rail 230 and the capsule 250 rotates about edge 250d as designated numeral 250C. Finally, as designated by numeral 250D, the capsules are arranged in the same direction so that the cap 250a is positioned forward. In this case, the capsule turns in the vertical plane.

On the other hand, in FIG. 6(c), the capsule 250 is contained in the bucket 220 so that the cap 250a is positioned forward. When the capsule 250 proceeds to the cutting part 231 of the guide fall 230, it rotates about edge 250e as designated by numeral 250F. Thus, the capsule 250 stands up so that the body is below the cap. The capsule 250 is conveyed in the bucked, the body 250b contacts the guide rail 230, and the capsule 250 is rotated as designated by numeral 250G. Finally, as designated by numeral 250H, the capsules are arranged in the same direction so that the cap 250a is positioned forward. The length L of the buckets 220 is made longer than the length of the capsule 250 in view of the rotation of the capsule 250.

In the conventional appearance examination apparatus for solid articles shown in FIG. 5, the solid articles 1 are held in the vertical direction by the examination head 200 which is intermittently rotated in the horizontal plane. For supplying the solid articles 1 to the examination head 200 in the vertical direction, the buckets 220 must be driven in the vertical direction by the chain mechanism and the like. As a result, the number of arrays of the solid article 1 which are supplied to the examination head 200 is limited to one line. The conventional appearance examination apparatus has a disadvantage that it is not possible for a large number of the solid articles to be examined by the apparatus in a unit of time.

Furthermore, the transfer of the solid article 1 between the bucket 220 and the examination head 200 is executed in the horizontal direction, so that a natural fall by gravity cannot be used. Therefore, it is necessary that the bucket 220 is stopped in synchronism with the intermittent rotation of the examination head 200, and that the plunger 221 is driven for forcibly transferring the solid article 1 to the examination head 200 from the bucket 220 during the period of time in which the bucket 220 and the examination head 200 are stopped. However, since the examination head 200, the buckets 220 and the plunger 221 are independently driven, it is necessary to synchronize their motions. As a result, the driving mechanisms of the examination head 200, the buckets 220, and the plunger 221 become complex and the driving speeds are slow.

On the other hand, in the conventional arranging apparatus shown in FIG. 6, there is a possibility that the capsule 250 turns in the vertical plane in the bucket 220. At that time, the capsule 250 irregularly rotates around the edges 250c, 250d of the cap 250a as a fulcrum. Thus, the positions of the capsules 250 in the buckets 220 are not fixed. That is, the intervals of the solid articles (capsules) which are conveyed by the buckets 220 are not constant. This disadvantage renders another problem that the solid article (capsule) needs to be detected when it reaches at a predetermined position and the plunger 221 is driven after detecting the solid article. As a result, the driving mechanisms of the examination head 200, the buckets 220, and the plunger 221 become more complex and the driving speeds are much slower.

SUMMARY OF THE INVENTION

It is an object of this invention to solve the above mentioned problems, and to provide an appearance examination apparatus for solid articles which has a simple configuration and a plurality of feeding lines of the solid articles.

An appearance examination apparatus for solid articles of this invention comprises:

a hopper for containing the solid articles;

an arranging apparatus for arranging the solid articles supplied from the hopper in a plurality of feeding lines, the solid articles arranged in the horizontal direction in the same manner;

an examination drum which is intermittently rotated in a predetermined direction around a horizontal axis in the vertical plane;

a plurality of sets of first and second examination rollers disposed in the vicinity of an outer periphery of the examination drum, one of the first and second examination rollers having the same number of positioning parts as the feeding lines of the solid articles, both of the first and second examination rollers being rotated in the same direction, and the solid articles held in the positioning parts being rotated in the opposite direction of the rotation direction of the first and second examination rollers; and at least one image pick-up device disposed in the vicinity of the outer periphery of the examination drum, the image pick-up device picking-up images of outer surfaces of the solid articles held in the positioning parts between the first and second examination rollers.

In the above-mentioned configuration, it is preferable that each positioning part has a pair of brims disposed at a distance substantially equal to a predetermined length of the solid articles to be examined.

Furthermore, it is preferable that the image pick-up device is a line sensor or a two-dimensional sensor.

Furthermore, it is preferable that the examination drum stops while the solid article held by the first and second examination rollers is rotated more than one turn.

When the solid article is a capsule having a body and a cap, it is preferable that the arranging apparatus comprises:

a feeding drum rotating around a first horizontal axis and having an arrangement of a plurality of first pockets for holding the solid articles in a manner so that the axis of each of the solid articles is perpendicular to the first horizontal axis;

a first restriction drum disposed below the feeding drum, the first restriction drum rotating around a second horizontal axis, and has an arrangement of a plurality of second pockets corresponding to the first pockets, each of the second pocket holding the solid article which is dropped with the body forward substantially perpendicular to the second horizontal axis in order not to protrude from the surface of the first restriction drum and holding the solid article which is dropped cap forward substantially perpendicular to the second horizontal axis in order to protrude from the surface, and the second pocket having a width able to hold the solid article substantially parallel to the second horizontal axis;

a first restriction guide disposed in the vicinity of an outer periphery of the first restriction drum, the first restriction guide contacting the solid articles protruding from the surface of the first restriction drum for dropping the solid articles sideways in a predetermined direction into the second pocket;

a second restriction drum disposed below the first restriction drum, the second restriction drum rotating around a third horizontal axis and has an arrangement of a plurality of third pockets corresponding to the second pockets, each of the third pockets holding the solid article which is dropped substantially horizontally from the second pocket and holding the solid article which is dropped cap forward substantially perpendicular to the third axis in order to protrude from the surface of the second restriction drum, the third pocket having a width for being able to hold the solid article substantially parallel to the third horizontal axis; and a second restriction guide disposed in the vicinity of the outer periphery of the second restriction drum, the second restriction guide contacting the solid articles protruding from the surface of the second restriction drum for dropping the solid articles sideways in a predetermined direction in the third pocket.

Furthermore, it is preferable that the arranging apparatus is disposed above the examination drum in the vertical direction, and the solid articles conveyed to the lowest part of the arranging apparatus are transferred to the examination drum by blowing compressed air.

In the appearance examination apparatus described above, the arranging apparatus arranges the solid articles which are supplied from the hopper in the same manner on a plurality of lines in the horizontal direction. The arranged solid articles are supplied to the positioning parts between the first and second examination rollers which are provided on the examination drum. Thus, the number of the solid articles supplied in a unit time increases. Since the examination drum is intermittently driven, it temporarily stops with respect of the other elements. During this stop period, the solid articles which are held by the first and second examination rollers rotate more than one turn, so that the image pick-up device can observe the entire surface of the solid articles.

Since the positioning part is configured by a pair of brims provided at a distance substantially equal to the standard length of the solid articles which are to be examined, when the solid article is longer than the standard length, it is impossible to hold the longer solid article between the two brims. Thus, the longer solid article is removed as an inferior or defective article before the appearance examination. On the other hand, when the solid article is shorter than the standard length, it is not properly positioned in the positioning part. The shorter solid article is judged as an inferior or defective article by the appearance examination apparatus. Furthermore, even though the length of the solid article is within the predetermined range of an excellent article, when extraneous material is adhered to the surface of the solid article, or when the surface of the solid article is uneven, the reflected light from the abnormal part changes. As a result, the solid article is judged as an inferior or defective article by the appearance examination apparatus.

As mentioned above, the appearance examination apparatus of this invention is configured to supply the solid articles arranged in the same manner in the horizontal direction to the examination drum by the arranging apparatus, to hold the solid articles which are rotated by the first and second examination roller at predetermined positions, and the rotated surfaces of the solid articles are observed by the image pick-up device. As a result, a plurality of solid articles on a plurality of feeding lines can be examined by one examination drum. Therefore, the number of the solid articles which are examined in a unit of time can largely be increased. Furthermore, when the solid articles are transferred to the examination drum from the arranging apparatus, not only gravity but also the compressed air are used. Thus, any special reciprocal mechanism such as a plunger which is used in the conventional apparatus are not needed in this invention. As a result, the configuration of the appearance examination apparatus for solid article of this invention becomes simple, and the driving speed of the appearance examination apparatus can be made fast. Furthermore, the solid articles are supplied at predetermined intervals, it is not necessary to detect the reach of the solid articles at predetermined positions, so that the configuration of the appearance examination apparatus for solid articles of this invention can be made much simpler.

DETAILED DESCRIPTION OF THE INVENTION

Figure 1:
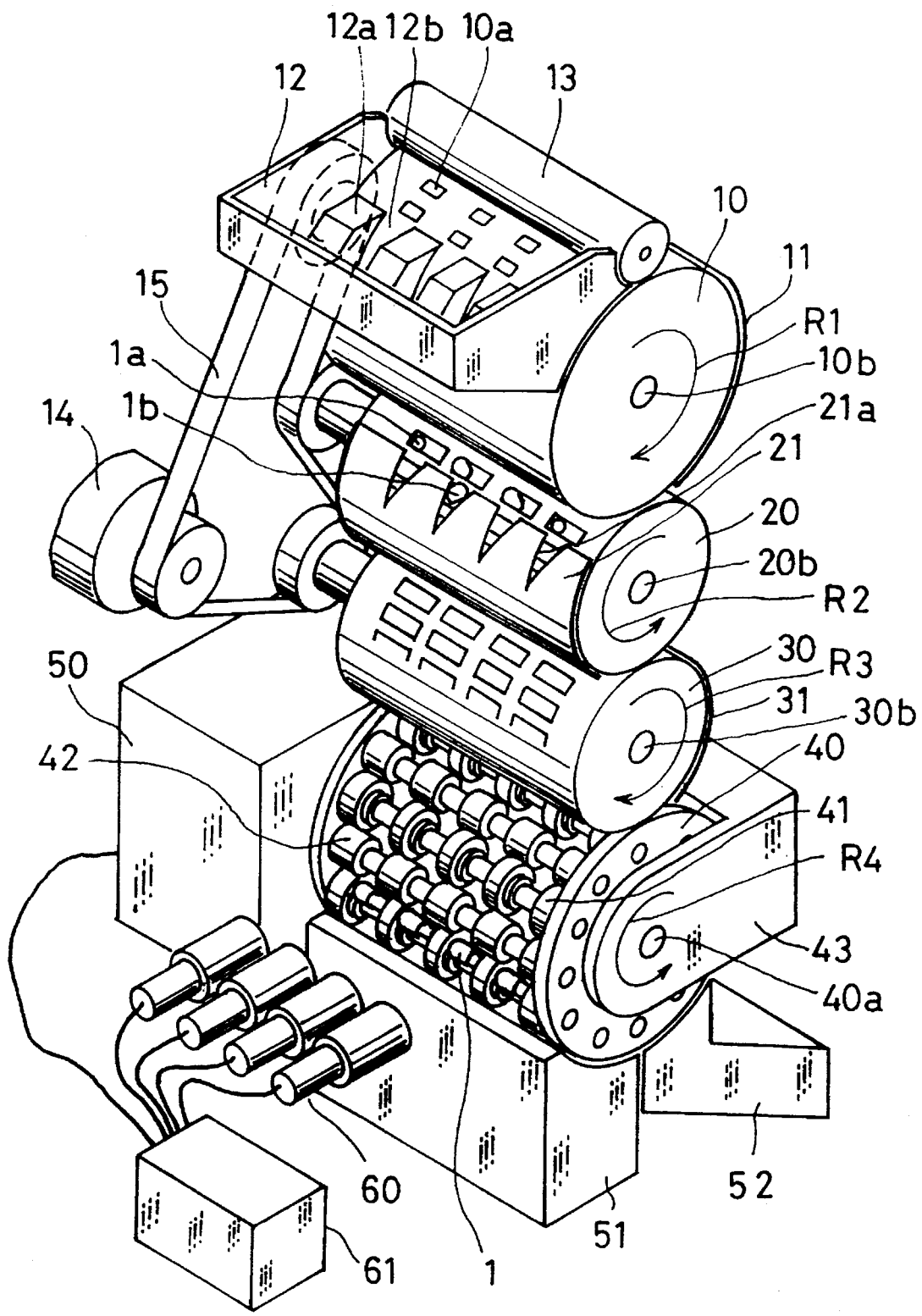
FIG. 1 is a perspective view showing a configuration of a preferred embodiment of an appearance examination apparatus for solid article of this invention.
Figure 2:
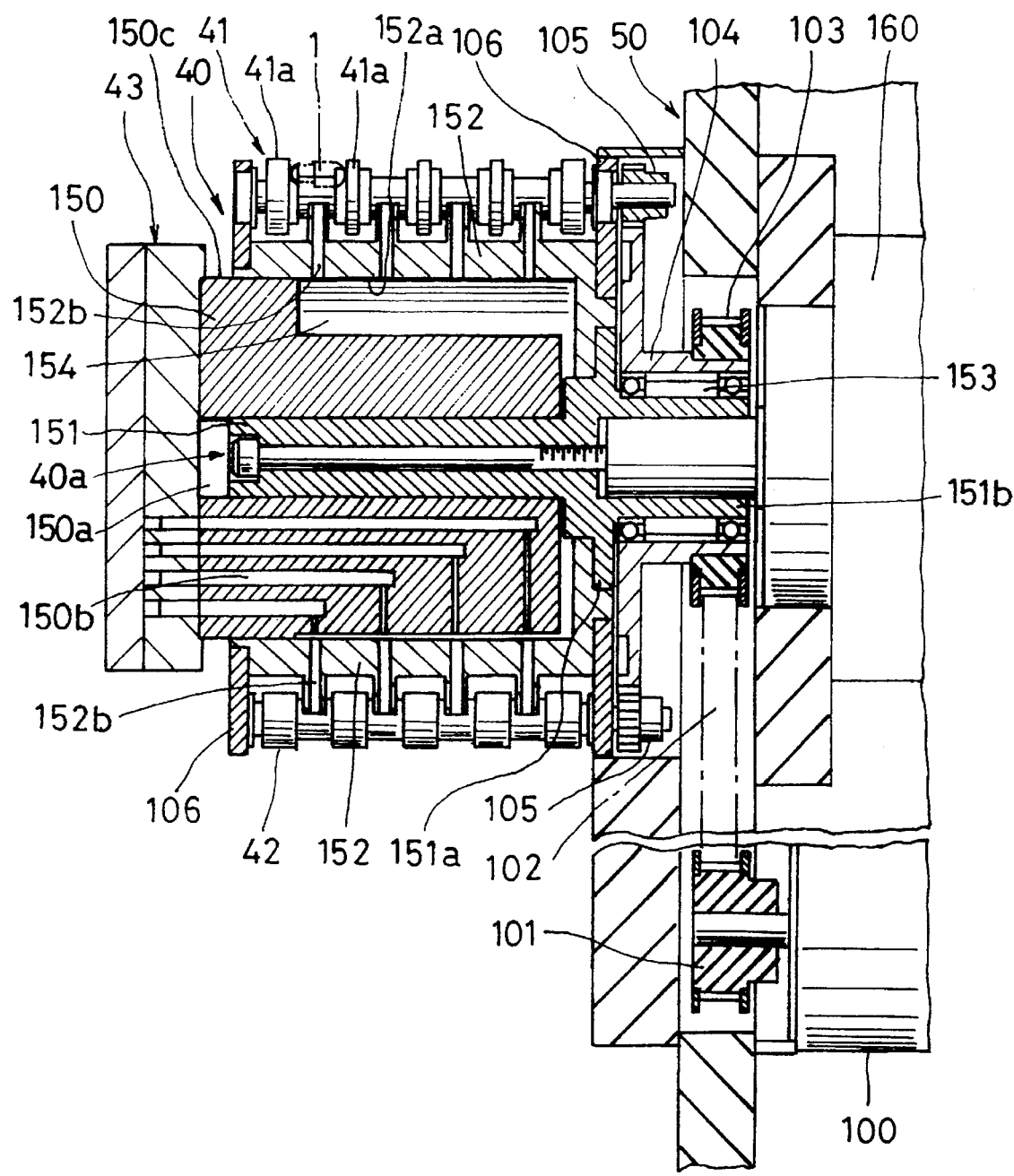
FIG. 2 is a sectional side view showing a detailed configuration of an examination drum 40 of FIG. 1.
Figure 3:
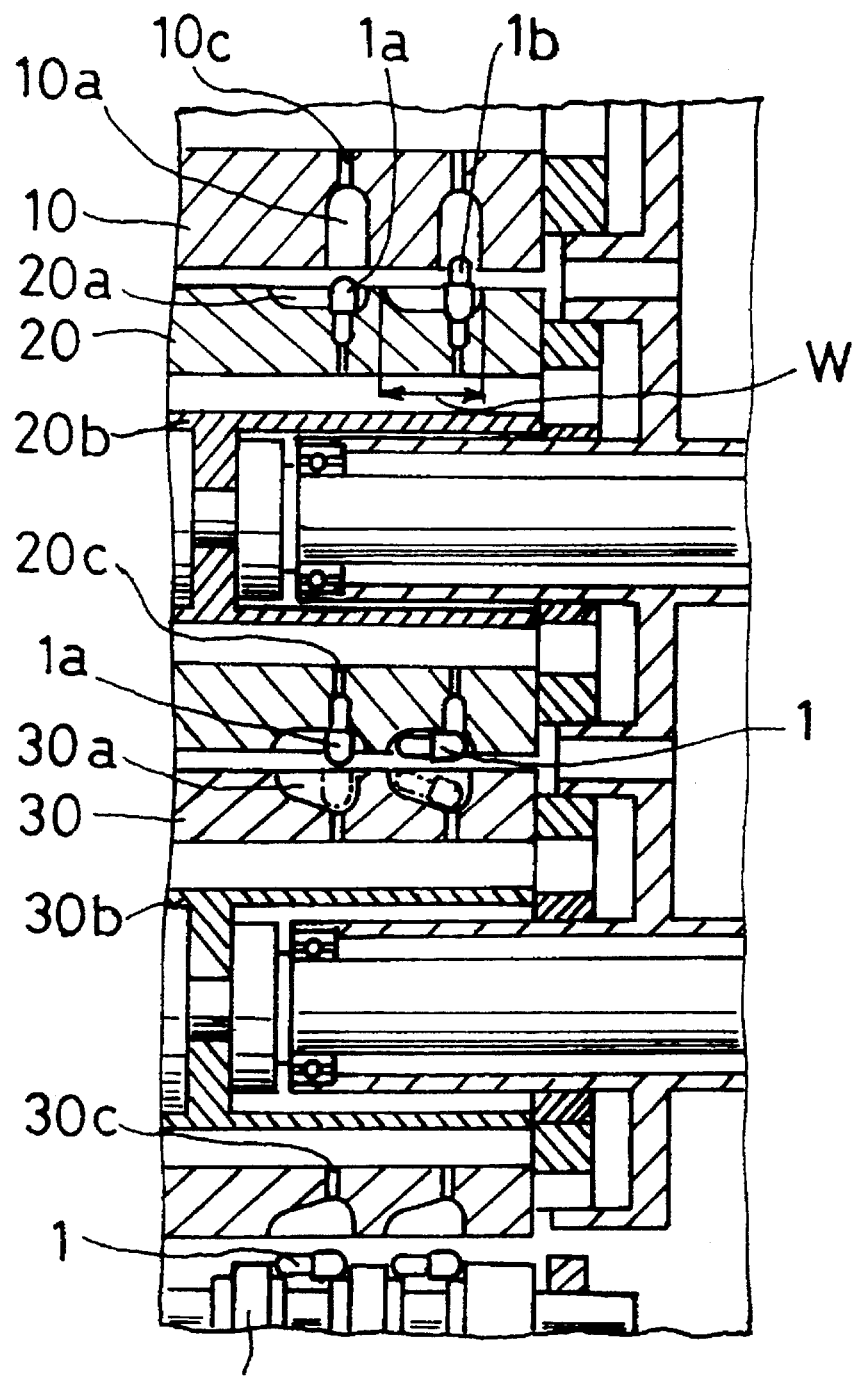
FIG. 3 is a sectional side view showing a detailed configuration of an arranging apparatus of FIG. 1.
Figure 4:
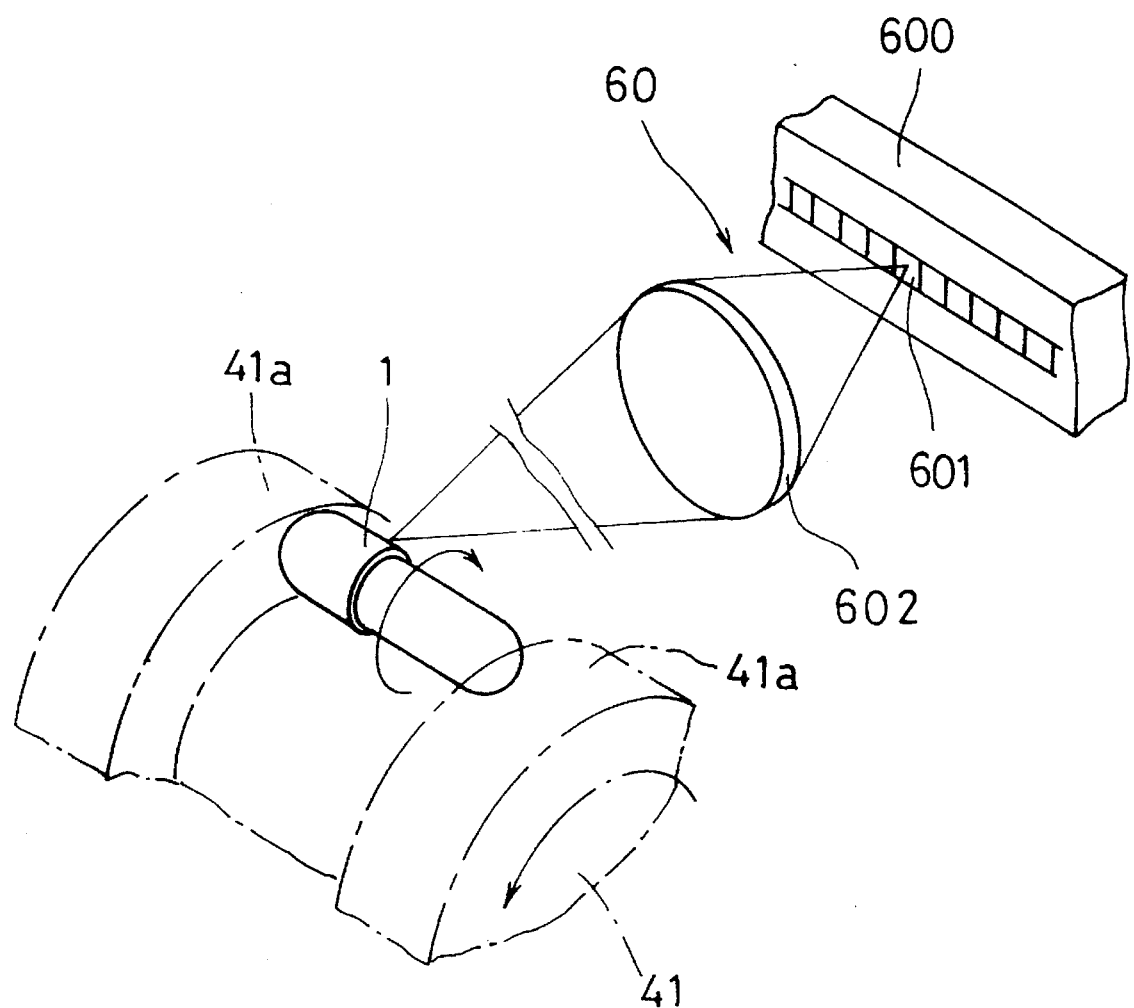
FIG. 4 is a perspective view showing an optical system for observing a surface of a solid article by an image pick-up device of tills invention.
Figure 5:
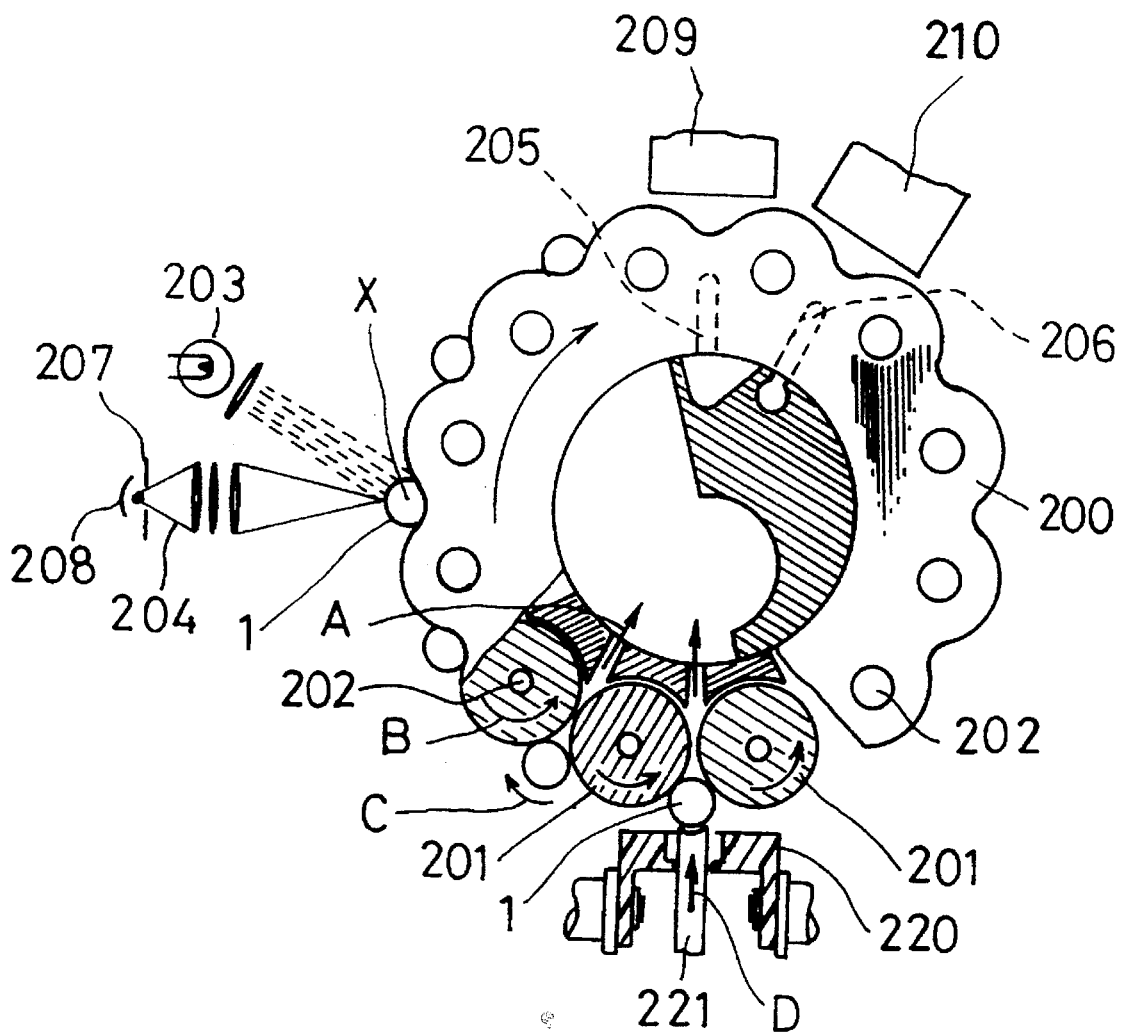
FIG. 5 is a plan view showing the configuration of the conventional appearance examination apparatus for solid article.
Figure 6A:
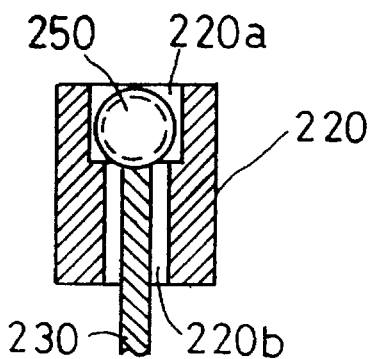
FIG. 6(a) is a sectional front view showing the configuration of the bucket 220 of the conventional arranging apparatus for solid article.
Figure 6B:
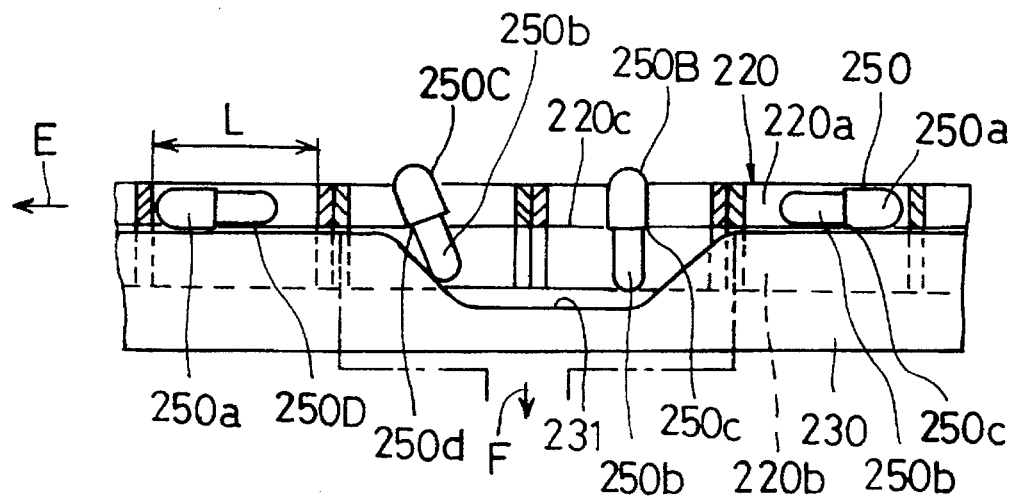
FIGS. 6(b) and 6(c) are sectional side views showing the configuration of the conventional arranging apparatus and the motions of the capsules in the conventional arranging apparatus.
Figure 6C:
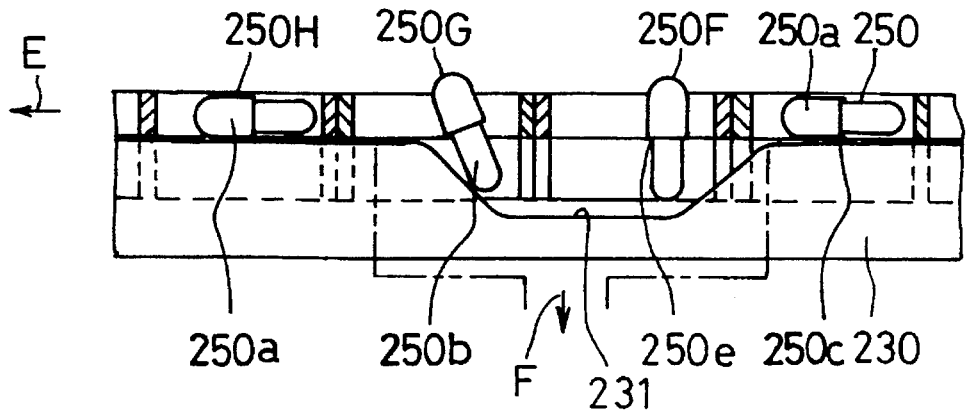

The appearance examination apparatus for solid article of this invention is described referring to FIGS. 1 to 4 which show a preferred embodiment of the invention. FIG. 1 is a perspective view showing a configuration of a preferred embodiment of an appearance examination apparatus for solid article of this invention. FIG. 2 is a sectional side view showing a detailed configuration of an examination drum 40 of FIG. 1. FIG. 3 is a sectional side view showing a detailed configuration of an arranging apparatus of FIG. 1. FIG. 4 is a perspective view showing an optical system for observing a surface of a solid article by an image pick-up device of this invention.

In the appearance examination apparatus for solid article shown in FIG. 1, a feeding drum 10 is rotated at a predetermined speed in the direction shown by arrow R1 in the vertical plane around a first horizontal axis 10b by a driving mechanism comprised of a motor 14, a timing belt 15, and the like. A hopper 12 and a brush 13 are provided above the feeding drum 10 and in the vicinity of an outer periphery of the feeding drum 10. The hopper 12 contains a large number of solid articles. The brush 13 removes superfluous solid articles on the outer periphery of the feeding drum 10. A plurality of first pockets 10a are regularly arranged on the cylindrical outer surface. As shown in FIG.3, each first pocket 10a holds the solid article 1 in a manner so that the lengthwise direction of the solid article 1 which has the largest size or length is substantially perpendicular to the first horizontal axis 10b. As shown in FIG. 1, a feeding guide 11 is provided in the vicinity of the outer periphery of the feeding drum 10 with a predetermined gap in order not to drop the solid articles held in the first pockets 10a. On the bottom of the hopper 12, a plurality of guides 12a are provided. When vibrations are applied to the hopper 12, the solid articles contained in the hopper 12 (which are not illustrated in the figure) will be arranged in grooves 12b between the guides 12a. The pitch or position of the grooves 12b coincide with the pitch or arrangement of the first pockets 10a.

A first restriction drum 20 is provided below the feeding drum 10, which rotates in the direction shown by arrow R2, opposite the rotation direction of the feeding drum 10 around a second horizontal axis 20b. A plurality of second pockets 20a (shown in FIG. 3) which face the first pockets 10a are arranged on the cylindrical surface of the first restriction drum 20. The rotation speed of the first restriction drum 20 is controlled by the timing belt 15 and the like in a manner so that the motions of the first pockets 10a and the second pockets 20a are synchronized. When the solid article 1 is a capsule comprising a body 1b and a cap 1a, as shown in FIG. 3, the second pocket 20a holds the solid article 1 which drops body forward (the body part of the capsule is below the cap part) from the first pocket 10 substantially perpendicular to the second horizontal axis 20b in order not to protrude from the surface of the first restriction drum 20. The second pocket 20a holds the solid article 1 which falls cap forward (the cap part of the capsule is below the body part) from the first pocket 10 substantially perpendicular to the second horizontal axis 20b in order to protrude from the surface of the first restriction drum 20. Furthermore, the second pocket 20a has width W in the horizontal direction sufficient to hold the solid article so that the axis of the solid article is substantially parallel to the second horizontal axis 20b.

A first restriction guide 21 is provided in the vicinity of the outer periphery of the first restriction drum 20 with a predetermined gap. A plurality of V-letter shaped cuttings 21a corresponding to the arrangement of the second pockets 20a are provided on the first restriction guide 21. The solid article 1 (body forward) which protrudes from the surface of the first restriction drum 20 contacts the edge of the cutting 21, so that it drops sideways in a direction substantially parallel to the second horizontal axis 20b. On the other hand, the solid article 1 (cap forward) which does not protrude from the surface of the first restriction drum 20 does not contact the edge of the cutting 21, so that it is guided in order not to drop from the second pocket 20a by the other part of the first restriction guide 21.

A second restriction drum 30 is provided below the first restriction drum 20, which rotates in the direction designated by arrow R3, opposite to the rotation direction of the first restriction drum 20, around a third horizontal axis 30b. A plurality of third pockets 30a (shown in FIG. 3) which face the second pockets 20a are arranged on the cylindrical surface of the second restriction drum 30. The rotation speed of the second restriction drum 30 is controlled by the timing belt 15 and the like in a manner so that the motions of the second pockets 20a and the third pockets 30a are synchronized. As shown in FIG. 3, the third pocket 30a holds the solid article 1 which drops substantially horizontally from the second pocket 20s, as shown in the figure a little slanted. The third pocket 30a holds the solid article 1 which falls cap forward from the second pocket 20a substantially perpendicular to the third horizontal axis 30b in order to protrude from the surface of the second restriction drum 30. Furthermore, the third pocket 30a has a width in the horizontal direction sufficient to holds the solid article in a manner so that the axis of the solid article is substantially parallel to the third horizontal axis 30b.

A second restriction guide 31 is provided in the vicinity of the outer periphery of the second restriction drum 30 with a predetermined gap. A plurality of V-letter shaped cuttings (not shown in the figure) which are similar to the cuttings 21 of the first restriction guide 21 are provided on the second restriction guide 31. The solid article which protrudes from the surface of the second restriction drum 30 contacts the edge of the cutting (not shown in the figure), so that it drops sideways substantially parallel to the third horizontal axis 30b. On the other hand, the solid article which does not protrude from the surface of the second restriction drum 30 does not contact the edge of the cutting, so that it is guided in order not to drop from the third pocket 30a by the other part of the second restriction guide 31. As a result, all solid articles are held substantially horizontal and the same manner in the third pockets 30a below the cuttings of the second restriction guide 31. An arranging apparatus of the appearance examination apparatus for solid articles of this invention is comprises the feeding drum 10, the feeding guide 11, the first restriction drum 20, the first restriction guide 21, the second restriction drum 30, the second restriction guide 31 and the like.

Connection tubes 10c, 20c and 30c, which are perpendicular to the horizontal rotation axes 10b, 20b and 30b, respectively, are provided in the first, second and third pockets 10a, 20a and 30a. During the conveyance of the solid articles 1, the air in the pockets 10a, 20a and 30a is removed by a vacuum through the connection tubes 10c, 20c and 30c, so that the solid articles 1 are held in the pockets 10a, 20a and 30a. In contrast, when the solid articles are reached to the lowest position of the drums 10, 20 and 30, compressed air is blown at the solid articles 1 through the communication tubes 10c, 20c and 30c. As a result, the solid articles 1 are certainly transferred to the next drum.

As shown in FIG. 1, an examination drum 40 is provided below the second restriction drum 40. The examination drum 40 intermittently rotates in the direction shown by arrow R4 around a fourth horizontal axis 40a. A plurality of first and second examination rollers 41 and 42, which have different shapes, are provided at predetermined angles or intervals in the vicinity of an outer periphery of the examination drum 40. One first examination roller 41 and one second examination roller 42 are a pair. The solid articles arranged in a predetermined manner by the arranging apparatus are held by a pair of first and second examination rollers 41 and 42 which are provided on the examination drum 40, and are intermittently conveyed on the outer periphery of the examination drum 40. The first and second examination rollers 41 and 42 rotate in a predetermined direction by a rotation mechanism which will be described in detail after. The solid articles 1 receive the reaction force of the rotation of the first and second examination rollers 41 and 42, so that they rotate in the opposite direction of the rotation of the examination rollers 41 and 42.

In the vicinity of the examination drum 40, an image pick-up device 60 for imaging or observing the appearance surfaces of the solid articles 1, a frame 43 for holding the examination drum 40 in the horizontal direction, a driving mechanism 50 for driving the examination drum 40, a controller 61 and the like are provided. Furthermore, an inferior or defective article remover 51 and a pick-up shoot 52 are provided below the examination drum 40. The inferior article remover 51 removes the inferior or defective articles which are determined to be inferior or defective by the image pick-up device 60 and the controller 61. Good articles which are not determined inferior or defective drop into the pick up shoot 52 to be conveyed to the next process. The stop time of the intermittent rotation of the examination drum 40 is longer than the time needed for the solid articles 1 to rotate one turn so that the entire outer surface of the solid article 1 can be observed by the image pick-up device 60.

A configuration of the examination drum 40 is described referring to FIG. 2. As shown in FIG. 2, a fixed axis 150 which does not rotate is held in the horizontal direction by the frame 43. An inner tube 150a which is provided on the center axis of the fixed axis 150 and a rotation axis 151 form a first bearing. An outer cylinder 150c and an inner tube 152a of an intermittent rotation member 152 which has a substantially cylindrical shape form a second bearing. The intermittent rotation member 152 is fixed on a flange part 151a of the rotation axis 151. Thus the intermittent rotation member 152 is rotatably borne in the horizontal direction by the first and second bearings. The intermittent rotation member 152 is coupled to an intermittent driving apparatus 160, and it is intermittently rotated with the rotation axis 151. At an end 151b of the rotation axis 151, which is not engaged with the fixed axis 150, a solar gear 104 is rotatably borne by a bearing 153. Flanges 106 are attached to both ends of the intermittent rotation member 152, and the first and second examination rollers 41 and 42 are rotatably borne by the flanges 106. Planet gears 105 are attached to an end of the first and second examination rollers 41 and 42, respectively, and the planet gears 105 are engaged with the solar gear 104. A pulley 103 is attached to the solar gear 104 and coupled to another pulley 101 which is attached to a motor 100 via a timing belt 102. As a result, the first and second examination rollers 41 and 42 rotate in a predetermined direction by the motor 100 independent from the intermittent rotation member 152.

A plurality of brims 41a are provided on the first examination roller 41. The distance between two brims 41a which face each other is substantially equal to a predetermined length of the solid articles to be examined with a predetermined tolerance. A plurality of nozzles 152b are provided on the intermittent rotation member 152. Positions of the nozzles 152b correspond to positions where the solid articles 1 are to be held between two brims 41a and are substantially centered between the first and second examination rollers 41 and 42. An air gap 154 between the intermittent rotation member 152 and the fixed axis 150 is connected to a vacuum pump (not shown in the figure). Thus, the solid articles 1 are held between the first and second examination rollers 41 and 42 by the vacuum. A plurality of air tubes 150b in the bottom part of the fixed axis 150, and the air tubes 150b are connected to an air compressor to supply compressed air.

When the inferior or defective solid article passes below the nozzle 152b, the compressed air is blown at the inferior solid article through the air tube 150b and the nozzle 152b. Thus, the inferior solid article is blown into the inferior article remover 51. The same mechanism is provided in another part of the fixed axis 150, and the good solid articles are blown into the pick-up shoot 52 to be conveyed to the next process.

Next, a relation for focusing the surface image of the solid article 1 on pixels of the image pick-up device 60 is described referring to FIG. 4. As shown in FIG. 4, the image pick-up device 60 comprises a line sensor 600 which comprises a charge coupled device (CCD) with 2048 pixels 601 and a lens 602. The solid article 1 is held between two brims 41a of the first examination roller 41. The solid article 1 is rotated in a predetermined direction. The surface of the solid article 1 is focused on the pixels 601 of the line sensor 600 by the lens 602. The line sensor 600 is driven by a predetermined clock, for example, 4 MHz. Each pixel 601 outputs an analog signal responding to the intensity of reflected light from corresponding each part of the surface of the solid article 1. The analog signals from the line sensor 600 are input to the controller 61 (shown in FIG. 1) and converted analog to digital signals (A/D conversion) and compared with predetermined reference signals. When extraneous material is adhered to the surface of the solid article 1, or when the surface of the solid article 1 is uneven, the reflected light from the abnormal part changes. Thus, by comparing the signals corresponding to the parts from which the reflected lights have changed and the predetermined reference signals, the inferiority or defectiveness of the solid article 1 can be detected. The solid article 1 is rotated more than one turn when the examination drum 40 (shown in FIG. 1) stops so that the image pick-up device 60 observes the entire surface of the solid article 1. If, the length of the solid article 1 (capsule) is short, the pixels 601 of the line sensor 600 not corresponding to the shorter solid article do not receive the reflected lights from the surface of the solid article 1. Since there is no output signals from the pixels or the output is very small, the shortness of the solid article 1 can be detected.

When the controller 61 detects the inferiority or defectiveness of the appearance of the solid article 1, the controller 61 outputs an information corresponding to the position of the inferior solid article to the driving apparatus 50. When the inferior solid article reaches to the inferior article remover 51, the driving apparatus 50 blows the compressed air at the inferior solid article through the air tube 150b, and the nozzle 152b. Thereby, the appearance examination of the solid articles 1 is completed and the good solid articles are conveyed to the next process, such as a PTP packaging apparatus through the pick-up shoot 52.

In the above-mentioned embodiment, the line sensor such as CCD is used in the image pick-up device 60. However, it is possible to use a two-dimensional sensor of CCD in the image pick-up device 60. In this case, the shape of the solid article 1 can be identified. Furthermore, the conventional sensor comprising a slit having a predetermined shape and a photocell can be used in the image pick-up device 60. An image pick-up device comprising a plurality of image sensors having a small image field can be used. In such a case, each image sensor corresponds to one feeding line of the solid articles. Or, an image sensor having a large image field covering a plurality of solid articles can be used. Furthermore, in the above-mentioned embodiment, the capsules containing preparations are examined. However, the appearance examination apparatus for solid article of this invention can examine the appearance of empty capsules which are not filled.

The invention may be embodied in other specific forms without departing from the spirit and scope thereof. The embodiments are to be considered in all respects as illustrative and not restrictive. The scope of the invention is indicated by the appended claims rather than by the foregoing description, and all changes which come within the meaning and range of equivalency of the claims are intended to be embraced therein.

What is claimed is:

1. An apparatus for examining the external appearance of solid articles, comprising: a hopper for containing said solid articles; an arranging apparatus for arranging said solid articles supplied from said hopper in a plurality of feeding lines, said solid articles arranged in a horizontal direction;

an examination drum which is intermittently rotated in a predetermined direction around a horizontal axis in a vertical plane;

a plurality of sets of first and second examination rollers rotatably borne on said examination drum in a vicinity of an outer periphery of said examination drum in a manner so that rotation axes of said first and second examination rollers are disposed on a circle which is coaxial with a rotation axis of said examination drum, one of said first and second examination rollers having same number of positioning parts as said feeding lines of said solid articles, a direction of rotation of both of said first and second examination rollers being the same, and a direction of rotation of said solid articles held in said positioning parts being opposite to said direction of rotation of said first and second examination rollers, said plurality of sets of first and second examination rollers are revolved along said circle by the rotation of said examination drum; and at least one image pick-up device disposed in the vicinity of the outer periphery of said examination drum, said image pick-up device picking-up images of outer surfaces of said solid articles held in said positioning parts between said first and second examination rollers.

2. The apparatus for examining the external appearance of solid articles in accordance with claim 1, wherein each positioning part has a pair of brims provided at a distance substantially equal to a predetermined length of said solid articles to be examined.

3. The apparatus for examining the external appearance of solid articles in accordance with claim 1 or 2, wherein said image pick-up device comprises a line sensor or a two-dimensional sensor.

4. The apparatus for examining the external appearance of solid articles in accordance with claim 1 or 2, wherein said examination drum stops while said solid article held by said first and second examination rollers is rotated more than one turn.

5. The apparatus for examining the external appearance of solid articles in accordance with claim 1 or 2, wherein said solid article is a capsule having a body and a cap, said arranging apparatus comprises:

a feeding drum rotating around a first horizontal axis and having an arrangement of a plurality of first pockets for holding said solid articles in a manner so that an axis of each of said solid articles is perpendicular to said first horizontal axis;

a first restriction drum disposed below said feeding drum, said first restriction drum rotating around a second horizontal axis and has an arrangement of a plurality of second pockets corresponding to said first pockets, each of said second pocket holding said solid article which is dropped with said body forward substantially perpendicular to said second horizontal axis in order not to protrude from the surface of said first restriction drum and holding said solid article which is dropped cap forward substantially perpendicular to said second horizontal axis in order to protrude from the surface, said second pocket having a width able to hold said solid article substantially parallel to said second horizontal axis;

a first restriction guide disposed in the vicinity of an outer periphery of said first restriction drum, said first restriction guide contacting said solid articles protruding from the surface of said first restriction drum for dropping said solid articles sideways in a predetermined direction into said second pocket;

a second restriction drum disposed below said first restriction drum, said second restriction drum rotating around a third horizontal axis and has an arrangement of a plurality of third pockets corresponding to said second pockets, each of said third pockets holding said solid article which is dropped substantially horizontally from said second pocket and holding said solid article which is dropped cap forward substantially perpendicular to said third axis in order to protrude from the surface of said second restriction drum, said third pocket having a width for being able to hold said solid article substantially parallel to said third horizontal axis; and a second restriction guide disposed in the vicinity of the outer periphery of said second restriction drum, said second restriction guide contacting said solid articles protruding from the surface of said second restriction drum for dropping said solid articles sideways in a predetermined direction into said third pocket.

6. The apparatus for examining the external appearance of solid articles in accordance with claim 5, wherein said arranging apparatus disposed above said examination drum in the vertical direction and said solid articles conveyed to a lowest part of said arranging apparatus are transferred to said examination drum by blowing compressed air.

7. The apparatus for examining the external appearance of solid articles in accordance with claim 1, wherein said examination drum comprises a pair of flanges, and said first and second examination rollers are rotatably borne between said flanges in a manner so that the rotation axes of said first and second examination rollers are in parallel with the rotation axis of said examination drum;

planet gears are respectively attached to an end of said first and second examination rollers, and said planet gears are engaged with a solar gear which is continuously rotated around the axis of said examination drum by a motor; and said examination drum is intermittently driven by a intermittent driving apparatus independently from the rotation of said first and second examination rollers.

8. The apparatus for examining the external appearance of solid articles in accordance with claim 7, wherein said examination drum has an inner tube part which is engaged with a fixed shaft, and has a plurality of nozzles provided at positions facing said solid articles which are held between said first and second examination rollers; and said fixed shaft has a plurality of air tubes in a predetermined part thereof in order to supply compressed air selectively through one of said nozzles for blowing off an inferior solid article.

* * * * *